United States Patent
Hansen et al.

(10) Patent No.: US 9,533,106 B2
(45) Date of Patent: Jan. 3, 2017

(54) TORSION-SPRING BASED WIND-UP AUTO INJECTOR PEN WITH DIAL-UP/DIAL-DOWN MECHANISM

(71) Applicant: Novo Nordisk A/S, Bagsvaerd (DK)

(72) Inventors: Torben S. Hansen, Lyngby (DK); Hans Hemmingsen, Birkeroed (DK); Christian H. Nielsen, Copenhagen NV (DK); Ebbe Kiilerich, Copenhagen NV (DK); Mikkel Avlund, Soeborg (DK); Matias Melander, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 93 days.

(21) Appl. No.: 14/368,708

(22) PCT Filed: Dec. 20, 2012

(86) PCT No.: PCT/EP2012/076421
§ 371 (c)(1),
(2) Date: Jun. 25, 2014

(87) PCT Pub. No.: WO2013/098194
PCT Pub. Date: Jul. 4, 2013

(65) Prior Publication Data
US 2014/0350478 A1    Nov. 27, 2014

Related U.S. Application Data

(60) Provisional application No. 61/587,435, filed on Jan. 17, 2012.

(30) Foreign Application Priority Data

Dec. 29, 2011   (EP) .................................... 11195986

(51) Int. Cl.
A61M 5/315    (2006.01)
A61M 5/20     (2006.01)
A61M 5/31     (2006.01)

(52) U.S. Cl.
CPC ............. *A61M 5/3156* (2013.01); *A61M 5/20* (2013.01); *A61M 5/2033* (2013.01);
(Continued)

(58) Field of Classification Search
CPC ..................... A61M 5/31545; A61M 5/31555; A61M 5/3156; A61M 5/31578; A61M 5/31593; A61M 5/2033
See application file for complete search history.

(56) References Cited

U.S. PATENT DOCUMENTS

| 854,390 A | 5/1907 | Bridge |
|---|---|---|
| 2,392,196 A | 1/1946 | Smith |

(Continued)

FOREIGN PATENT DOCUMENTS

| AU | 595723 | 1/1988 |
|---|---|---|
| AU | 2003232576 A1 | 1/2004 |

(Continued)

OTHER PUBLICATIONS

Annersten, M. et al., Insulin Pens Dribble From the Tip of the Needle After Injection, Practical Diabetes Int., vol. 17(4), pp. 109-111 (2000).

(Continued)

*Primary Examiner* — Andrew Gilbert
(74) *Attorney, Agent, or Firm* — Wesley Nicolas

(57) ABSTRACT

The present invention relates to an automatic torsion spring based injection device having a dial-up/dial-down mechanism by which a dose can be set by rotating a dose setting member in a first direction and which dose size can be (Continued)

reduced by rotating the same dose setting member in a second and opposite direction. The dial-up/dial-down mechanism operates a torsion spring which is strained when setting a dose and unstained when rotating the dose setting element in the second direction. In order to secure the torsion spring when strained, a ratchet arm (21) following the rotation of the dose setting element in the first direction, engages a toothed element (10) such that engagement of the at least one ratchet arm (21) with teeth (12) of the toothed element (10) prevents unwinding of the torsion spring, and wherein the rotation of the dose setting member in the first direction moves the ratchet arm (21) from one tooth (12) to the subsequent tooth (12) of the toothed element (10), and rotation of the dose setting member in the second direction lowering the set dose activates the ratchet arm (21) to disengage the teeth (12) of the toothed element (10) and thereby allow the torsion spring to move the ratchet arm (21) in the second direction to the previous tooth (12) such that the force accumulated in the torsion spring reduces incrementally. In order to provide a smooth movement when dialing down the set dose, the at least one ratchet arm (21) is provided o a ratchet tube (20) which carries friction teeth (30) which engage with a cam curve (16) of the toothed element, dampening the movement of the ratchet arm (21) by the torsion spring.

5 Claims, 5 Drawing Sheets

(52) U.S. Cl.
CPC ...... *A61M 5/3155* (2013.01); *A61M 5/31578* (2013.01); *A61M 5/31593* (2013.01); *A61M 5/31535* (2013.01); *A61M 5/31553* (2013.01); *A61M 2005/3126* (2013.01); *A61M 2005/3143* (2013.01); *A61M 2205/42* (2013.01)

(56) References Cited

U.S. PATENT DOCUMENTS

| | | | |
|---|---|---|---|
| 2,956,563 A | 10/1960 | Sarnoff | |
| 3,110,310 A | 11/1963 | Cislak | |
| 3,115,135 A | 12/1963 | Sarnoff | |
| 3,144,178 A | 8/1964 | Sarnoff, Et Al. | |
| 3,556,099 A | 1/1971 | Knight et al. | |
| 3,729,003 A | 4/1973 | Hurschman | |
| 3,880,162 A | 4/1975 | Simmons | |
| 3,944,843 A | 3/1976 | Vaz Martins | |
| 4,026,288 A | 5/1977 | Costa et al. | |
| 4,231,368 A | 11/1980 | Becker | |
| 4,275,727 A | 6/1981 | Keeri-Szanto | |
| 4,277,227 A | 7/1981 | Jenkins | |
| 4,298,000 A | 11/1981 | Thill et al. | |
| 4,300,554 A | 11/1981 | Hessberg et al. | |
| 4,313,439 A | 2/1982 | Babb et al. | |
| 4,314,556 A | 2/1982 | Ma | |
| 4,368,731 A | 1/1983 | Schramm | |
| RE31,315 E | 7/1983 | Jenkins et al. | |
| 4,393,723 A | 7/1983 | Brand | |
| 4,430,079 A | 2/1984 | Thill et al. | |
| 4,465,478 A | 8/1984 | Sabelman et al. | |
| 4,470,317 A | 9/1984 | Sabloewski et al. | |
| 4,493,704 A | 1/1985 | Beard et al. | |
| 4,498,904 A | 2/1985 | Turner et al. | |
| 4,515,584 A | 5/1985 | Abe et al. | |
| 4,568,335 A | 2/1986 | Updike et al. | |
| 4,584,439 A | 4/1986 | Paddock | |
| 4,585,439 A | 4/1986 | Michel | |
| 4,634,431 A | 1/1987 | Whitney et al. | |
| 4,676,122 A | 6/1987 | Szabo et al. | |
| 4,749,109 A | 6/1988 | Kamen | |
| 4,812,724 A | 3/1989 | Langer et al. | |
| 4,833,379 A | 5/1989 | Kaibel et al. | |
| 4,838,860 A | 6/1989 | Groshong et al. | |
| 4,865,591 A | 9/1989 | Sams | |
| 4,871,351 A | 10/1989 | Feingold | |
| 4,883,472 A | 11/1989 | Michel | |
| 4,893,291 A | 1/1990 | Bick et al. | |
| 4,898,578 A | 2/1990 | Rubalcaba, Jr. | |
| 4,919,596 A | 4/1990 | Slate et al. | |
| 4,924,737 A | 5/1990 | Gummow | |
| 4,936,833 A | 6/1990 | Sams | |
| 4,950,246 A | 8/1990 | Muller | |
| 4,973,318 A | 11/1990 | Holm et al. | |
| 4,988,337 A | 1/1991 | Ito | |
| 4,994,033 A | 2/1991 | Shockey et al. | |
| 4,998,922 A | 3/1991 | Kuracina et al. | |
| 5,000,744 A | 3/1991 | Hoffman et al. | |
| 5,002,537 A | 3/1991 | Hoffman et al. | |
| 5,011,479 A | 4/1991 | Le et al. | |
| 5,064,098 A | 11/1991 | Hutter, III et al. | |
| 5,078,698 A | 1/1992 | Stiehl et al. | |
| 5,104,380 A * | 4/1992 | Holman | A61M 5/20 604/117 |
| 5,104,388 A | 4/1992 | Quackenbush | |
| 5,112,317 A | 5/1992 | Michel | |
| 5,113,869 A | 5/1992 | Nappholz et al. | |
| 5,114,406 A | 5/1992 | Gabriel et al. | |
| 5,122,317 A | 6/1992 | Chen et al. | |
| 5,135,485 A | 8/1992 | Cohen et al. | |
| 5,154,698 A | 10/1992 | Compagnucci et al. | |
| 5,163,904 A | 11/1992 | Lampropoulos et al. | |
| 5,176,646 A | 1/1993 | Kuroda | |
| 5,207,752 A | 5/1993 | Sorenson et al. | |
| 5,221,268 A | 6/1993 | Barton et al. | |
| 5,226,342 A | 7/1993 | Panin | |
| 5,226,895 A | 7/1993 | Harris | |
| 5,226,896 A | 7/1993 | Harris | |
| 5,244,461 A | 9/1993 | Derlien | |
| 5,244,465 A | 9/1993 | Michel | |
| 5,246,417 A | 9/1993 | Haak et al. | |
| 5,257,987 A | 11/1993 | Athayde et al. | |
| 5,271,527 A | 12/1993 | Haber et al. | |
| 5,279,585 A | 1/1994 | Balkwill | |
| 5,279,586 A | 1/1994 | Balkwill | |
| 5,281,198 A | 1/1994 | Haber et al. | |
| 5,284,480 A | 2/1994 | Porter et al. | |
| 5,292,976 A | 3/1994 | Dessau et al. | |
| 5,295,976 A | 3/1994 | Harris | |
| 5,304,152 A | 4/1994 | Sams | |
| 5,308,340 A | 5/1994 | Harris | |
| 5,314,412 A | 5/1994 | Rex | |
| 5,318,540 A | 6/1994 | Athayde et al. | |
| 5,320,609 A | 6/1994 | Haber et al. | |
| 5,331,954 A | 7/1994 | Rex et al. | |
| 5,368,572 A | 11/1994 | Shirota | |
| 5,370,629 A | 12/1994 | Michel et al. | |
| 5,378,233 A | 1/1995 | Haber et al. | |
| 5,383,856 A | 1/1995 | Bersin | |
| 5,383,865 A | 1/1995 | Michel | |
| 5,440,976 A | 8/1995 | Giuliano et al. | |
| 5,445,606 A | 8/1995 | Haak et al. | |
| 5,447,150 A | 9/1995 | Bacon | |
| 5,478,316 A | 12/1995 | Bitdinger et al. | |
| 5,480,387 A | 1/1996 | Gabriel et al. | |
| 5,492,534 A | 2/1996 | Athayde et al. | |
| 5,496,286 A | 3/1996 | Stiehl et al. | |
| 5,505,697 A | 4/1996 | McKinnon, Jr. et al. | |
| 5,505,704 A | 4/1996 | Pawelka et al. | |
| 5,514,097 A | 5/1996 | Knauer | |
| 5,536,249 A | 7/1996 | Castellano et al. | |
| 5,546,932 A | 8/1996 | Galli | |
| 5,549,575 A | 8/1996 | Giambattista et al. | |
| 5,573,729 A | 11/1996 | Belgardt et al. | |
| 5,582,598 A | 12/1996 | Chanoch | |
| 5,584,815 A | 12/1996 | Pawelka et al. | |
| 5,591,136 A | 1/1997 | Gabriel | |
| 5,593,390 A | 1/1997 | Castellano et al. | |
| 5,599,314 A | 2/1997 | Neill | |

(56) References Cited

U.S. PATENT DOCUMENTS

| | | |
|---|---|---|
| 5,611,783 A | 3/1997 | Mikkelsen |
| 5,611,784 A | 3/1997 | Barresi et al. |
| 5,626,566 A | 5/1997 | Petersen et al. |
| 5,628,309 A | 5/1997 | Brown |
| 5,637,095 A | 6/1997 | Nason et al. |
| 5,645,052 A | 7/1997 | Kersey |
| 5,662,612 A | 9/1997 | Niehoff |
| 5,674,204 A | 10/1997 | Chanoch |
| 5,679,111 A | 10/1997 | Hjertman et al. |
| 5,681,285 A | 10/1997 | Ford et al. |
| 5,685,864 A | 11/1997 | Shanley et al. |
| 5,688,251 A | 11/1997 | Chanoch |
| 5,709,662 A | 1/1998 | Olive et al. |
| 5,716,990 A | 2/1998 | Bagshawe et al. |
| 5,720,733 A | 2/1998 | Brown |
| 5,725,508 A | 3/1998 | Chanoch et al. |
| 5,728,074 A | 3/1998 | Castellano et al. |
| 5,728,559 A | 3/1998 | Nilsson et al. |
| 5,741,211 A | 4/1998 | Renirie et al. |
| 5,743,889 A | 4/1998 | Sams |
| 5,755,692 A | 5/1998 | Manicom |
| 5,782,633 A | 7/1998 | Muhlbauer |
| 5,807,334 A | 9/1998 | Hodosh et al. |
| 5,814,022 A | 9/1998 | Antanavich et al. |
| 5,820,602 A | 10/1998 | Kovelman et al. |
| 5,823,998 A | 10/1998 | Yamagata |
| 5,827,232 A | 10/1998 | Chanoch et al. |
| 5,830,194 A | 11/1998 | Anwar et al. |
| 5,843,036 A | 12/1998 | Olive et al. |
| 5,879,360 A | 3/1999 | Crankshaw |
| 5,879,630 A | 3/1999 | Lescouzeres et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,933,671 A | 8/1999 | Stephany et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,954,700 A | 9/1999 | Kovelman |
| 5,957,889 A | 9/1999 | Poulsen et al. |
| 5,961,496 A | 10/1999 | Nielsen et al. |
| 5,971,963 A | 10/1999 | Choi |
| 5,980,491 A | 11/1999 | Hansen |
| 5,984,900 A | 11/1999 | Mikkelsen |
| 5,989,221 A | 11/1999 | Hjertman |
| 5,998,989 A | 12/1999 | Lohberg |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,019,745 A | 2/2000 | Gray |
| 6,033,376 A | 3/2000 | Rockley |
| 6,033,377 A | 3/2000 | Rasmussen et al. |
| 6,036,675 A | 3/2000 | Thorne et al. |
| 6,048,336 A | 4/2000 | Gabriel |
| 6,074,372 A | 6/2000 | Hansen |
| 6,083,197 A | 7/2000 | Umbaugh |
| 6,086,567 A | 7/2000 | Kirchhofer et al. |
| 6,096,010 A | 8/2000 | Walters et al. |
| 6,110,148 A | 8/2000 | Brown et al. |
| 6,110,149 A | 8/2000 | Klitgaard et al. |
| 6,129,080 A | 10/2000 | Pitcher et al. |
| 6,146,361 A | 11/2000 | DiBiasi et al. |
| 6,159,161 A | 12/2000 | Hodosh |
| 6,161,364 A | 12/2000 | Kolberg |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 | 5/2001 | Steenfeldt-Jensen et al. |
| 6,245,046 B1 | 6/2001 | Sibbitt |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,268,722 B1 | 7/2001 | Kogure et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,364,860 B1 | 4/2002 | Steck et al. |
| 6,379,339 B1 | 4/2002 | Klitgaard et al. |
| 6,383,167 B2 | 5/2002 | Kirchhofer et al. |
| 6,391,005 B1 | 5/2002 | Lum et al. |
| 6,419,661 B1 | 7/2002 | Kuhr et al. |
| 6,514,230 B1 | 2/2003 | Munk et al. |
| 6,537,251 B2 | 3/2003 | Klitmose |
| 6,547,755 B1 | 4/2003 | Himbert et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,585,698 B1 | 7/2003 | Packman et al. |
| 6,599,272 B1 | 7/2003 | Hjertman et al. |
| 6,605,067 B1 | 8/2003 | Larsen |
| 6,613,019 B2 | 9/2003 | Munk |
| 6,663,602 B2 | 12/2003 | Møller |
| 6,666,849 B1 | 12/2003 | Marshall et al. |
| 6,673,033 B1 | 1/2004 | Sciulli et al. |
| 6,692,472 B2 | 2/2004 | Hansen et al. |
| 6,699,224 B2 | 3/2004 | Kirchhofer et al. |
| 6,716,198 B2 | 4/2004 | Larsen |
| 6,726,661 B2 | 4/2004 | Munk et al. |
| 6,752,798 B2 | 6/2004 | McWethy et al. |
| 6,770,288 B2 | 8/2004 | Duirs |
| 6,796,970 B1 | 9/2004 | Klitmose et al. |
| 6,852,404 B2 | 2/2005 | Kuwajima et al. |
| 6,887,238 B2 | 5/2005 | Jahns et al. |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,080,936 B1 | 7/2006 | Simpson |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,133,329 B2 | 11/2006 | Skyggebjerg et al. |
| 7,175,055 B2 | 2/2007 | Hansen et al. |
| 7,195,609 B2 | 3/2007 | Huegli |
| 7,195,616 B2 | 3/2007 | Diller et al. |
| 7,241,278 B2 | 7/2007 | Moller |
| 7,500,966 B2 | 3/2009 | Hommann |
| 7,678,084 B2 | 3/2010 | Judson et al. |
| 7,686,786 B2 * | 3/2010 | Moller ............ A61M 5/14566 604/134 |
| 7,704,238 B2 | 4/2010 | Diller et al. |
| 7,771,399 B2 | 8/2010 | Burren et al. |
| 8,048,037 B2 | 11/2011 | Kohlbrenner et al. |
| 8,202,256 B2 | 6/2012 | Moller |
| 8,206,361 B2 | 6/2012 | Moller |
| 8,267,899 B2 | 9/2012 | Moller |
| 8,870,831 B2 * | 10/2014 | Holmqvist ........ A61M 5/31553 604/135 |
| 9,132,239 B2 * | 9/2015 | Moller ............ A61M 5/31525 |
| 2001/0016571 A1 | 8/2001 | Ohkubo et al. |
| 2001/0034506 A1 | 10/2001 | Hirschman et al. |
| 2001/0053893 A1 | 12/2001 | Larsen |
| 2002/0002326 A1 | 1/2002 | Causey et al. |
| 2002/0002354 A1 | 1/2002 | Vetter et al. |
| 2002/0007154 A1 | 1/2002 | Hansen et al. |
| 2002/0020654 A1 | 2/2002 | Eilersen |
| 2002/0049415 A1 | 4/2002 | Fukuda |
| 2002/0052578 A1 | 5/2002 | Moller |
| 2002/0077852 A1 | 6/2002 | Ford et al. |
| 2002/0107486 A1 | 8/2002 | Munk |
| 2002/0120235 A1 | 8/2002 | Enggaard |
| 2002/0165500 A1 | 11/2002 | Bechtold et al. |

(56) References Cited

U.S. PATENT DOCUMENTS

| | | |
|---|---|---|
| 2002/0173752 A1 | 11/2002 | Polzin |
| 2002/0188250 A1 | 12/2002 | Landau et al. |
| 2003/0009133 A1 | 1/2003 | Ramey |
| 2003/0039679 A1 | 2/2003 | Duirs |
| 2003/0040715 A1 | 2/2003 | D'Antonio et al. |
| 2003/0050609 A1 | 3/2003 | Sams |
| 2003/0073954 A1 | 4/2003 | Moberg et al. |
| 2003/0114800 A1 | 6/2003 | Veasey et al. |
| 2003/0172924 A1 | 9/2003 | Staniforth et al. |
| 2003/0176871 A1 | 9/2003 | Pavlov et al. |
| 2003/0216663 A1 | 11/2003 | Jersey-Willuhn et al. |
| 2003/0233075 A1 | 12/2003 | Huegli |
| 2004/0010204 A1 | 1/2004 | Weber et al. |
| 2004/0024361 A1 | 2/2004 | Fago et al. |
| 2004/0051368 A1 | 3/2004 | Caputo et al. |
| 2004/0054326 A1 | 3/2004 | Hommann et al. |
| 2004/0059299 A1 | 3/2004 | Moller |
| 2004/0097879 A1 | 5/2004 | Woolston |
| 2004/0108339 A1 | 6/2004 | Hansen et al. |
| 2004/0158304 A1 | 8/2004 | Cory et al. |
| 2004/0171983 A1 | 9/2004 | Sparks et al. |
| 2004/0186431 A1 | 9/2004 | Graf et al. |
| 2004/0199117 A1 | 10/2004 | Giambattista et al. |
| 2004/0207385 A1 | 10/2004 | Gafner et al. |
| 2004/0210199 A1 | 10/2004 | Atterbury et al. |
| 2004/0230157 A1 | 11/2004 | Perry et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2004/0267208 A1 | 12/2004 | Veasey et al. |
| 2005/0004529 A1 | 1/2005 | Veasey et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0090782 A1 | 4/2005 | Marshall et al. |
| 2005/0197625 A1 | 9/2005 | Haueter et al. |
| 2005/0205083 A1 | 9/2005 | Staniforth et al. |
| 2005/0209570 A1 | 9/2005 | Moller |
| 2005/0268915 A1 | 12/2005 | Wassenaar et al. |
| 2006/0118612 A1 | 6/2006 | Christoffersen et al. |
| 2006/0258988 A1 | 11/2006 | Keitel et al. |
| 2006/0264838 A1 | 11/2006 | Volckmann et al. |
| 2007/0093761 A1 | 4/2007 | Veasey et al. |
| 2007/0167916 A1 | 7/2007 | Lee et al. |
| 2007/0244445 A1 | 10/2007 | Moller |
| 2007/0265568 A1 | 11/2007 | Tsals et al. |
| 2008/0065026 A1 | 3/2008 | Moller |
| 2008/0147005 A1* | 6/2008 | Moller .............. A61M 5/14566 604/134 |
| 2008/0221530 A1 | 9/2008 | Glejbol et al. |
| 2008/0281275 A1 | 11/2008 | Moller |
| 2008/0306445 A1* | 12/2008 | Burren .................. A61M 5/24 604/136 |
| 2008/0312592 A1 | 12/2008 | Barrow-Williams et al. |
| 2009/0043264 A1 | 2/2009 | Glejbol et al. |
| 2009/0062748 A1 | 3/2009 | Moller et al. |
| 2011/0046565 A1 | 2/2011 | Radmer et al. |
| 2012/0095410 A1* | 4/2012 | Moller .............. A61M 5/31525 604/207 |
| 2012/0209208 A1* | 8/2012 | Stefanski ................ A61M 5/20 604/189 |
| 2013/0204197 A1 | 8/2013 | Bicknell et al. |
| 2013/0274676 A1* | 10/2013 | Ekman ................ A61M 5/2033 604/197 |
| 2015/0148750 A1* | 5/2015 | Pedersen ................ A61M 5/20 604/207 |

FOREIGN PATENT DOCUMENTS

| | | | |
|---|---|---|---|
| BR | P10613926 A2 | 2/2011 | |
| CA | 2359375 A1 | 7/2000 | |
| CN | 1214292 A | 4/1999 | |
| DE | 3048135 A1 | 7/1982 | |
| DE | 3236374 A1 | 4/1984 | |
| DE | 3609555 A1 | 9/1987 | |
| DE | 3638984 A1 | 5/1988 | |
| DE | 3923079 A1 | 1/1991 | |
| DE | 4223958 A1 | 1/1993 | |
| DE | 4419235 A1 | 12/1995 | |
| DE | 19503230 A1 | 8/1996 | |
| DE | 29513214 U1 | 1/1997 | |
| DE | 19723647 C1 | 12/1998 | |
| DE | 19838760 A1 | 4/2000 | |
| DE | 29907880 U1 | 9/2000 | |
| DE | 10103287 A1 | 8/2001 | |
| DE | 20209051 U1 | 4/2003 | |
| DE | 10201875 C1 | 5/2003 | |
| DE | 10229122 A1 | 2/2004 | |
| DE | 10237258 A1 | 3/2004 | |
| DE | 20317377 U1 | 4/2005 | |
| DE | 102004046003 A1 | 3/2006 | |
| DK | 200100240 | 11/2001 | |
| DK | 2005/00116 U1 | 6/2005 | |
| EA | 008160 | 4/2007 | |
| EP | 15617 | 9/1980 | |
| EP | 017318 A1 | 10/1980 | |
| EP | 0064858 A1 | 11/1982 | |
| EP | 295075 | 12/1988 | |
| EP | 327810 A2 | 8/1989 | |
| EP | 327910 | 8/1989 | |
| EP | 338806 | 10/1989 | |
| EP | 0362484 A2 | 4/1990 | |
| EP | 387854 | 9/1990 | |
| EP | 422482 | 4/1991 | |
| EP | 454331 | 10/1991 | |
| EP | 498737 | 8/1992 | |
| EP | 879610 | 8/1992 | |
| EP | 608343 | 4/1993 | |
| EP | 554995 A1 | 8/1993 | |
| EP | 554996 | 8/1993 | |
| EP | 594349 | 4/1994 | |
| EP | 615762 | 9/1994 | |
| EP | 513128 | 7/1995 | |
| EP | 0673482 | 9/1995 | |
| EP | 679440 A1 | 11/1995 | |
| EP | 702970 | 3/1996 | |
| EP | 0704225 A2 | 4/1996 | |
| EP | 0708179 A2 | 4/1996 | |
| EP | 897728 | 2/1999 | |
| EP | 897729 A2 | 2/1999 | |
| EP | 908273 | 4/1999 | |
| EP | 0937471 | 8/1999 | |
| EP | 0937472 | 8/1999 | |
| EP | 937476 | 8/1999 | |
| EP | 1003581 | 8/1999 | |
| EP | 956873 A2 | 11/1999 | |
| EP | 1351732 | 1/2001 | |
| EP | 1074273 | 2/2001 | |
| EP | 1095668 A1 | 5/2001 | |
| EP | 1216717 A1 | 6/2002 | |
| EP | 1216719 A1 | 6/2002 | |
| EP | 1000631 | 7/2002 | |
| EP | 0747391 | 3/2004 | |
| EP | 1462134 A1 | 9/2004 | |
| EP | 1541185 | 6/2005 | |
| EP | 1557163 | 7/2005 | |
| EP | 1557189 A1 | 7/2005 | |
| EP | 1568389 | 8/2005 | |
| EP | 1304129 | 11/2005 | |
| EP | 1610848 A1 | 1/2006 | |
| EP | 1645301 | 4/2006 | |
| EP | 1723977 | 11/2006 | |
| EP | 1728529 | 12/2006 | |
| EP | 1768725 A1 | 4/2007 | |
| EP | 1782853 | 5/2007 | |
| EP | 1819382 | 8/2007 | |
| EP | 1909871 A1 | 4/2008 | |
| EP | 1926514 A1 | 6/2008 | |
| EP | 2000161 | 12/2008 | |
| EP | 2019701 A1 | 2/2009 | |
| EP | 2373361 A1 | 10/2011 | |
| FR | 2583291 | 12/1986 | |

(56) References Cited

FOREIGN PATENT DOCUMENTS

| | | |
|---|---|---|
| FR | 2622457 | 5/1989 |
| FR | 2697434 A1 | 5/1994 |
| FR | 2740345 | 4/1997 |
| FR | 2767479 | 2/1999 |
| FR | 2857654 | 1/2005 |
| GB | 574705 | 1/1946 |
| GB | 664044 | 1/1952 |
| GB | 2091107 | 7/1982 |
| GB | 2153445 | 8/1985 |
| GB | 2229497 | 9/1990 |
| GB | 2309644 | 8/1997 |
| GB | 0007071.4 | 3/2000 |
| IN | 165367 | 3/1986 |
| JP | 56-163486 | 12/1981 |
| JP | 57-000033 | 1/1982 |
| JP | 01-035671 A | 2/1989 |
| JP | 01-100495 | 4/1989 |
| JP | 02071758 A | 3/1990 |
| JP | 02-126184 | 5/1990 |
| JP | 02-182267 | 7/1990 |
| JP | 4-224764 | 8/1992 |
| JP | 04256757 A | 9/1992 |
| JP | 4-507059 | 12/1992 |
| JP | 05-337179 | 12/1993 |
| JP | 06-055644 | 1/1994 |
| JP | 06-034825 | 10/1994 |
| JP | 06-296691 | 10/1994 |
| JP | H07-500039 | 1/1995 |
| JP | 7-502678 | 3/1995 |
| JP | 09166474 | 6/1997 |
| JP | 11511364 | 10/1999 |
| JP | 3017167 | 11/1999 |
| JP | 2000237308 | 9/2000 |
| JP | 2002503122 | 1/2002 |
| JP | 2003284777 | 10/2003 |
| JP | 2004503303 A | 2/2004 |
| JP | 2004-516895 | 6/2004 |
| JP | 2004533285 A | 11/2004 |
| JP | 2005536300 A | 12/2005 |
| JP | 2006250582 | 9/2006 |
| JP | 2007-509662 | 4/2007 |
| JP | 2008-528071 A | 7/2008 |
| JP | 2008-196696 A | 8/2008 |
| PL | 1804865 | 10/2005 |
| PL | 2373361 | 9/2012 |
| RU | 2111019 | 5/1997 |
| RU | 2091087 | 9/1997 |
| RU | 2212254 | 9/2003 |
| RU | 2254878 C2 | 6/2005 |
| SU | 1528330 A3 | 12/1989 |
| WO | 8502256 | 5/1985 |
| WO | 8702895 A1 | 5/1987 |
| WO | 8907463 | 8/1989 |
| WO | 90/09202 | 8/1990 |
| WO | 9110460 A1 | 7/1991 |
| WO | 9110677 | 7/1991 |
| WO | 91/14467 A1 | 10/1991 |
| WO | 9301573 | 1/1993 |
| WO | 9303780 | 3/1993 |
| WO | 9307922 | 4/1993 |
| WO | 9412228 | 6/1994 |
| WO | 95/21645 A1 | 8/1995 |
| WO | 9524233 | 9/1995 |
| WO | 9607443 | 3/1996 |
| WO | 9626754 | 9/1996 |
| WO | 96/32973 | 10/1996 |
| WO | 9638190 | 12/1996 |
| WO | 9707841 | 3/1997 |
| WO | 9710865 A1 | 3/1997 |
| WO | 9730742 | 8/1997 |
| WO | 9734919 | 9/1997 |
| WO | 9736626 | 10/1997 |
| WO | 9810813 | 3/1998 |
| WO | 9856436 | 12/1998 |
| WO | 9856439 | 12/1998 |
| WO | 9857688 | 12/1998 |
| WO | 9907425 | 2/1999 |
| WO | 9915214 | 4/1999 |
| WO | 9916487 | 4/1999 |
| WO | 9921598 | 5/1999 |
| WO | 9938554 | 8/1999 |
| WO | 9948546 | 9/1999 |
| WO | 9965548 A1 | 12/1999 |
| WO | 0015224 A1 | 3/2000 |
| WO | 0037098 A1 | 6/2000 |
| WO | 0037129 | 6/2000 |
| WO | 00/51668 | 9/2000 |
| WO | 01/10484 | 2/2001 |
| WO | 01/19434 A1 | 3/2001 |
| WO | 0126710 | 4/2001 |
| WO | 01/30425 | 5/2001 |
| WO | 0172361 | 10/2001 |
| WO | 0195959 A1 | 12/2001 |
| WO | 0205876 | 1/2002 |
| WO | 0224257 | 3/2002 |
| WO | 02/50214 A2 | 6/2002 |
| WO | 02/053214 | 7/2002 |
| WO | 02064196 | 8/2002 |
| WO | 02/076535 | 10/2002 |
| WO | 02/076537 | 10/2002 |
| WO | 02076536 | 10/2002 |
| WO | 02/092153 A2 | 11/2002 |
| WO | 03/057285 A2 | 7/2003 |
| WO | 03/057286 A1 | 7/2003 |
| WO | 03057283 | 7/2003 |
| WO | 03063680 | 8/2003 |
| WO | 9733638 | 9/2003 |
| WO | 03080160 | 10/2003 |
| WO | 03099357 | 12/2003 |
| WO | 2004/002556 A1 | 1/2004 |
| WO | 2004004825 | 1/2004 |
| WO | 2004007002 A1 | 1/2004 |
| WO | 2004/024218 | 3/2004 |
| WO | 2004/028598 A1 | 4/2004 |
| WO | 2006/045529 | 4/2004 |
| WO | 2004035113 A2 | 4/2004 |
| WO | 2004054644 A1 | 7/2004 |
| WO | 2004/078240 | 9/2004 |
| WO | 2004/078242 A2 | 9/2004 |
| WO | 2004078239 A1 | 9/2004 |
| WO | 2004078241 | 9/2004 |
| WO | 2004080306 | 9/2004 |
| WO | 2004084795 | 10/2004 |
| WO | 2004/093940 A2 | 11/2004 |
| WO | 2004095379 | 11/2004 |
| WO | 2005018721 | 3/2005 |
| WO | 2005037352 | 4/2005 |
| WO | 2005/046770 | 5/2005 |
| WO | 2005089835 | 9/2005 |
| WO | 2005097233 | 10/2005 |
| WO | 2005097240 | 10/2005 |
| WO | 2005/102421 A1 | 11/2005 |
| WO | 2006/003130 A1 | 1/2006 |
| WO | 2006/26754 A2 | 3/2006 |
| WO | 2006/037434 A1 | 4/2006 |
| WO | 2006039930 A1 | 4/2006 |
| WO | 2006040296 A2 | 4/2006 |
| WO | 2006/045528 | 5/2006 |
| WO | 2006045425 | 5/2006 |
| WO | 2006045525 | 5/2006 |
| WO | 2006045526 A1 | 5/2006 |
| WO | 2006/069454 | 7/2006 |
| WO | 2006076921 | 7/2006 |
| WO | 2006116997 | 11/2006 |
| WO | 2006/128794 | 12/2006 |
| WO | 2007021195 A1 | 2/2007 |
| WO | 2007/030957 | 3/2007 |
| WO | 2007041843 | 4/2007 |
| WO | 2007063342 A1 | 6/2007 |
| WO | 2007104636 A1 | 9/2007 |
| WO | 2007107558 A2 | 9/2007 |
| WO | 2007107561 | 9/2007 |
| WO | 20071134954 | 11/2007 |
| WO | 2008/003130 A1 | 1/2008 |

(56) References Cited

FOREIGN PATENT DOCUMENTS

| WO | 2008/031239 | A1 | 3/2008 |
|---|---|---|---|
| WO | 2008/037801 | | 4/2008 |
| WO | 2008057223 | | 5/2008 |
| WO | 2010046394 | A1 | 4/2010 |
| WO | WO/2010/046394 | * | 4/2010 |
| WO | 2010089418 | A2 | 8/2010 |
| WO | 2011025448 | A1 | 3/2011 |
| WO | 2011136718 | A1 | 11/2011 |

OTHER PUBLICATIONS

Beckmann, Sensors, Memory, Circuits, Polyapply Newsletter, vol. 1(3), (2006).

Chia Kai Su et al, Process Biochemistry, 2006, vol. 41, Part 2, pp. 257-263.

Dennison, Clive et al, Protein Expression and Purification, 1997, vol. 11, Part 2, pp. 149-161.

Fransson et al, Pharmaceutical Research, 1997, vol. 14, Part 5, pp. 606-612.

Gnanalingham, M.G. et al., Accuracy and Reproducibility of Low Dose Insulin Administration Using Pen-Injectors and Syringes, Downloaded From adc.bmj.com on Jan. 9, 2008.

Leonil et al, Enzyme and Microbiol Technology, 1994, vol. 16, Part 7, pp. 591-595.

Paule, B.J.A. et al, Protein Expression and Purification, 2004, vol. 34, Part 2, pp. 311-316.

Trankler, Hans-Rolf, R. Oldenbourg, Verlag, Munchen, Wien, Taschenbuch Der Messtechnik, 1996.

Rose, Keith et al., Bioconjugate Chemistry, "Natural Peptides As Building Blocks for the Synthesis of Large Protein-Like Molecules With Hydrazone and Oxime Linkages", 1996, vol. 7, 2, pp. 552-556.

Yurkovetskiy, A. et al., Biomacromolecules., "Fully Degradable Hydrophilic Polyals for Protein Modification", 2005, vol. 6, 5, pp. 2648-2658.

* cited by examiner

TORSION-SPRING BASED WIND-UP AUTO INJECTOR PEN WITH DIAL-UP/DIAL-DOWN MECHANISM

CROSS-REFERENCE TO RELATED APPLICATIONS

This application is a 35 U.S.C. §371 National Stage application of International Application PCT/EP2012/076421 (published as WO 2013/098194), filed Dec. 20, 2012, which claimed priority of European Patent Application 11195986.2, filed Dec 29, 2011; this application claims priority under 35 U.S.C. §119 of U.S. Provisional Application 61/587,435; filed Jan. 17, 2012.

THE TECHNICAL FIELD OF THE INVENTION

The present invention relates to a dial-up/dial-down mechanism for automatic wind-up pens. In particular, the present invention relates to an integrated dial-up/dial-down mechanism for a torsion spring assisted wind-up pen. The invention further relates to an automatic torsion spring based injection device incorporating such dial-up/dial-down mechanism and to an automatic torsion spring device incorporating anti-rattling means.

DESCRIPTION OF RELATED ART

In known injection devices, such as wind-up pens, based on torsion springs, the user usually strains the torsion spring by rotating a rotatable dose setting member usually provided at an end of the injection device. The rotational force thereby applied by the user during dose setting is accumulated in the torsion spring for later release.

An example of a known wind-up pen applying a torsion spring may be found in U.S. Pat. No. 5,104,380. In this wind-up pen, the dose setting member is located at the proximal end and works such that when the user rotates the dose setting member the torsion spring is strained and maintained in this strained position until the user releases the set dose by activating the latch. The wind-up pen disclosed in U.S. Pat. No. 5,104,380 has the disadvantage that if a user set a dose which is larger than the intended dose there is no possibility for decreasing the set dose. The user then has to release the latch mechanism thereby expelling the entire set dose before a new correct dose can be set and delivered.

Wind-up pen in which the user can actually decrease the set dose is e.g. known from WO 2006/045526, WO 2007/063342, WO 2010/046394 and WO 2010/089418.

These automatic injection devices are based on a torsion spring which is tighten during dose setting and thereafter released to inject the set dose. If a user erroneously sets a dose higher than needed these injection devices has the possibility of lowering the set dose by rotating the dose setting member in an opposite rotational direction. Such dial-down mechanism can therefore save the user from expelling expensive drug due to an erroneous dose setting.

In WO 2006/045526 and in WO 2010/046394, the dial-up/dial-down mechanism is based on a flexible ratchet arm which is locked in a one-way engagement with a toothed ring. When the user sets a dose he rotates the flexible ratchet arm in a toothed arrangement such that the ratchet arm locks against the force of the torsion spring in the subsequent teeth of the toothed ring thereby straining the torsion spring in incremental steps. In order to reduce the set size, the flexible arm is pulled out of engagement with the toothed ring whereby the force accumulated in the torsion spring rotates the ratchet arm rapidly backwards such that the flexible arm engages the previous tooth in the toothed ring thereby lowering the set dose with one increment. A separate element is provided which when moved rotational engages and pulls the ratchet arm out of its engagement with the toothed ring. If the user continuously rotates the dose setting member in the dial-down direction, the ratchet arm will, under influence of the torsion spring, move downward in the toothed ring in a series of incremental steps.

A similar arrangement is disclosed in WO 2010/089418, however in the dial-up/dial-down mechanism of this injection device depictured in FIG. 2, the toothed element securing the ratchet arm against the force of the torsion spring has outwardly pointing teeth and the ratchet arm points toward the center axis of the injection device.

In the arrangement disclosed in WO 2007/063342, there are three ratchet arms depictured in FIG. 12 which engage a toothed ring provided in the drive gear thereby retaining the torsion spring in its strained position. These ratchet arms can deflect radially inwardly such that when a user wishes to reduce the set dose he simply rotates the dose setting member in the opposite direction.

A major problem in the above dial-up/dial-down mechanism is that when the user dials down the set dose he actually releases the torsion spring by forcing the ratchet arm out of engagement with the toothed element and the actual dial down i.e. the backward movement of the ratchet arm is performed by the torsion spring.

Automatic injection devices often operate with a pre-tensed torsion spring in order to operate in a range of the torsion spring characteristic where the torsion spring applies a relatively constant and a relatively large force. A result of this is that the backward movement of the ratchet arm performed by the spring appears rather coarse and rough. The feel when rotating the dose setting member in the dial-down direction is therefore somewhat uncomfortable.

DESCRIPTION OF THE INVENTION

It is an object of the present invention to provide a dial-up/dial-down mechanism for an automatic wind-up pen which overcomes the above and provides a more smoothly feel when dialing down the set dose.

Accordingly, in a first aspect, the invention relates to a dial-up/dial-down mechanism in an automatic torsion spring based injection device for multiple injections of a settable dose of a liquid drug. Such injection device comprises a housing securing a rotatable dose setting element by which a user can set the size of the dose to be injected.

By automatic is here meant that the injection devices encompassed a torsion spring which is strained during dose setting by rotating the dose setting element in one direction, and which spring during injection is released to drive the liquid drug out from the injection device via an attached injection needle.

Further, once a certain dose size is set it can be adjusted i.e. lowered by rotating the dose setting element in the opposite direction (opposite of the dose setting direction) which unstrains the torsion spring i.e. reduces the torque present in the torsion spring.

The dial-up/dial-down mechanism assists in setting and adjusting (i.e. lowering) the dose size. In order to secure the torsion spring in its tensed position a ratchet arm engages a toothed element which secures the ratchet arm from rotation in one direction. Obviously more than one ratchet arm can be provided all though here described in singularity. The ratchet arm is coupled to a dose setting element such that when the dose setting element is rotated in one direction to set a dose, the ratchet arm is moved in its engagement with the toothed element to a subsequent tooth whereby the torsion spring is incrementally strained. In order to decrease the set dose, means are provided for pulling the ratchet arm out of engagement with the toothed element such that the torque accumulated in the torsion spring can rotate the ratchet arm in the opposite direction where it is gripped by the previous teeth of the toothed element thereby incrementally decreasing the torque of the torsion spring and thus decreasing the dose size. In order to control and dampen the backward movement of the ratchet arm by the torsion spring, friction teeth are provided in the engagement between the ratchet tube carrying the ratchet arm and the toothed element.

When the ratchet arm is pulled out of engagement with the toothed element there is no engagement between the ratchet tube and the toothed element as such however the two parts are rotatable connected e.g. by a circular ridge on one element engaging a similar circular track on the other element which in itself creates some friction.

The friction teeth can be provided either on the ratchet tube or on the toothed element and provides a controlled friction which is larger than the friction that would normally be present when such two elements rotate in relation to each other. When elements rotate or otherwise move in relation to each other while being in contact some degree of friction will always occur. However, by "friction teeth" is meant the presence of special teeth which is designed to provide a controlled friction above the inherent friction.

It is obviously also possible to have friction teeth provided on both the ratchet tube and on the toothed element. The toothed element can e.g. be provided with a cam curve engaging the friction teeth on the ratchet tube thereby creating further friction. The cam curve could e.g. follow a traditional sinus curve or any suitable curve. If the friction teeth are provided on the toothed element, the cam curve can alternatively be provided on the ratchet tube.

As is disclosed in e.g. WO 2010/046394 and WO 2010/089418 a reset tube (in the latter referred to as a coupling sleeve) establishing contact between the dose setting button and the ratchet tube is preferably provided. The dose setting button can be integral with the reset tube if so wanted.

The ratchet tube can be formed integral with a dose indicator or it can itself be the dose indicator. In a further embodiment, a separate dose indicator sleeve can be provided. Such dose indicator sleeve is preferably keyed to the ratchet tube by a key and groove connection such that the dose indicator sleeve can rotate together with the ratchet tube but move axially in relation to the ratchet tube i.e. the dose indicator sleeve can slide axially as it rotates together with the ratchet tube. The simultaneous rotational and axial movement could e.g. be accomplished by having the dose indicator sleeve engaging a helical thread provided inside the housing. In order for the dose indicator sleeve to slide axially the tolerances of the key and groove connection most allow such axial movement.

This however creates the problem that the dose indicator sleeve can rattle during movement. In order to prevent such rattling, anti-rattling means such as a number of flexible legs is provided between the ratchet tube and the dose indicator sleeve.

In a second aspect, the invention relates to an automatic torsion spring based injection device for multiple injections of a settable dose of a liquid drug comprising; a housing holding the liquid drug, a rotatable dose setting element for setting the size of the dose, and the dial-up/dial-down mechanism herein described. The rotatable dose setting member strains and unstrains the torsion spring and is preferably rotatable secured to the housing either directly or through another component.

In a third aspect, the invention relates to a torsion spring based injection device incorporating the anti-rattle means described. Such torsion spring based injection device does not necessarily have to incorporate the frictions teeth disclosed above.

In an embodiment these anti-rattling means can be provided as flexible legs provided between the dose indicator sleeve and a ratchet tube. The flexible legs can be provided on either of the dose indicator sleeve or the ratchet tube abutting the other. Alternatively the legs can be provided on both elements abutting the other element.

DEFINITIONS

An "injection pen" is typically an injection apparatus or device having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the back-end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Further the term "injection needle" defines a piercing member adapted to penetrate the skin of a subject for the purpose of delivering or removing a liquid.

"Dose indicator sleeve" is preferably meant to be a cylinder shaped hollow element, somewhat like a sleeve of a shirt, carrying indicia indicating the size of the selected dose to the user of the injection pen. "Indicia" is meant to incorporate any kind of printing or otherwise provided symbols e.g. engraved or adhered symbols.

Using the term "Automatic" in conjunction with an injection device means that, the injection device is able to perform the injection without the user of the injection device delivering the force needed to expel the drug during dosing. The force is typically delivered—automatically—by automatic means such as an electric motor or a spring. The spring is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on the injection device to release the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the dial-up, dial-down mechanism including the ring shaped element 10 whereas the term "proximal end" is meant to refer to the opposite end pointing away from the ring shaped element 10.

The prior art dial down mechanism known from WO 2010/046394 is disclosed in FIG. 1 to FIG. 5.

It comprises three parts, a fixation element or ring 10, a dose setting element or ratchet tube 20 and a reset tube 40.

Figure 3:
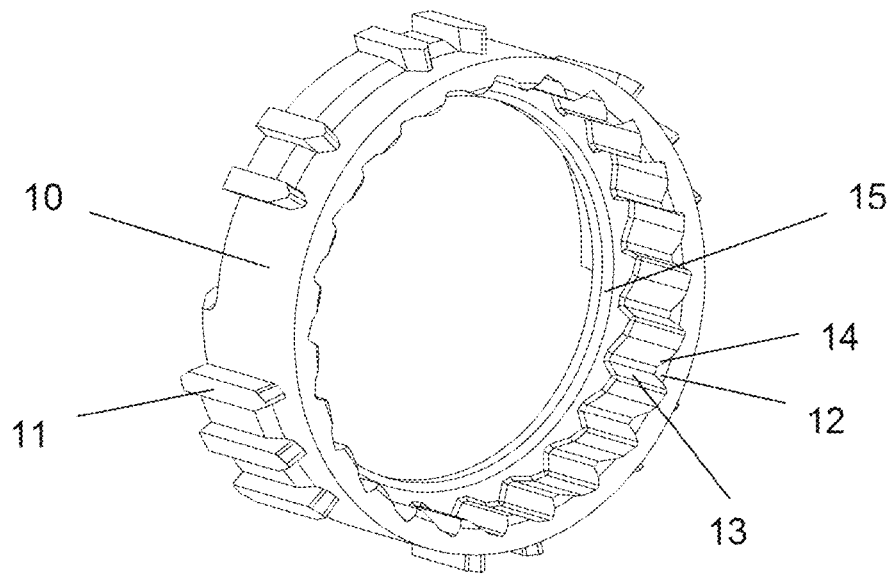
FIG. 3 show a view of the prior art fixation element in a ring-shaped configuration.

As seen in FIG. 3, the ring 10 which constitutes a part of the driving mechanism has on its outside surface a number of engaging means such as fins 11 by which the ring 10 is non-rotatable coupled to a not shown housing of an injection device. The ring 10 could alternatively be attached to the housing in a number of different ways, however, as explained later the ring shaped element 10 must be able to slide axially relatively to the housing in order to release the torque accumulated in the torsion spring.

Figure 2:
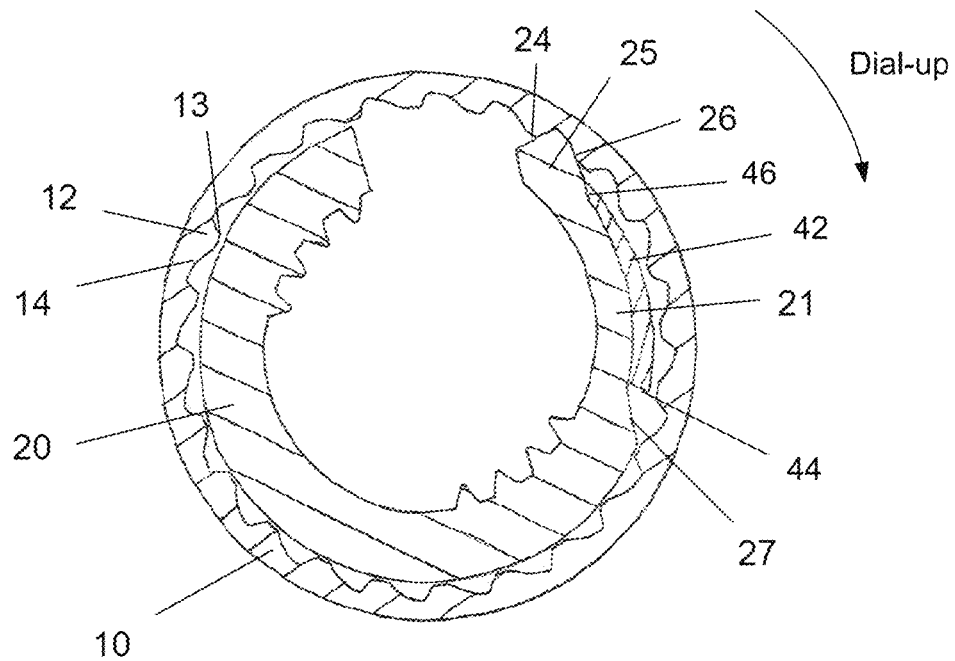
FIG. 2 show a sectional view of the dial-up/dial-down mechanism of FIG. 1.

The not-shown torsion spring is secured to the ratchet tube 20 at one end and to the housing at the other end such that the torsion spring is tightened whenever the ratchet tube 20 is rotated in the dial-up direction (see FIG. 2). The ratchet tube 20 is arranged such that it follows the rotation of the dose setting member when the user sets the dose to be delivered.

On its inside surface the ring 10 is provided with a plurality of teeth 12 which has a steep edge 13 in one direction and a sloped edge 14 in the opposite direction such that the ratchet arm 21 of the ratchet tube 20 is prevented from rotating in one direction but is allowed to rotate in the opposite direction. This is best seen in FIG. 2.

Figure 4:
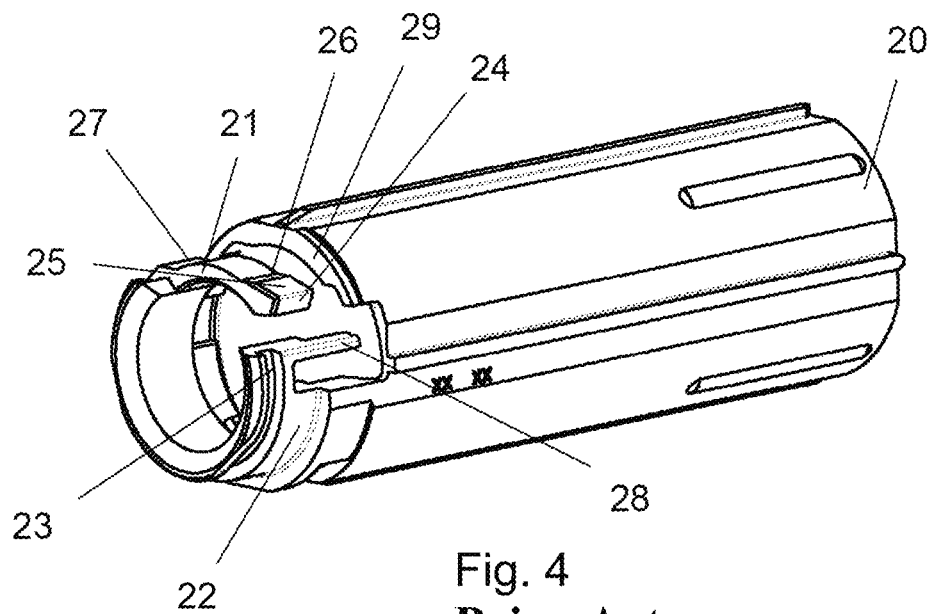
FIG. 4 show a view of the prior art ratchet tube.
Figure 5:
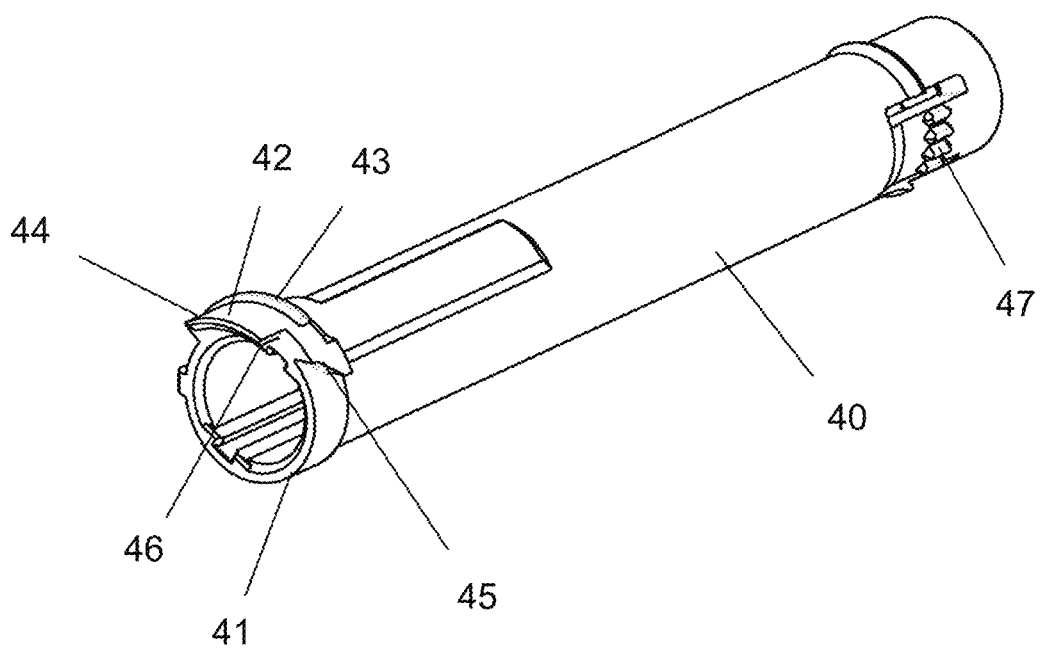
FIG. 5 show a view of the prior art reset tube.

The ratchet tube 20 disclosed in details on FIG. 4 has on its distal end a circular part with a peripheral outer surface 22 that fits into the inside of the ring 10. This outer surface 22 is provided with a circular recess 23 which is engaged with a similar circular element 15 on the ring 10 such that the ring 10 and the ratchet tube 20 is locked to each other in the axial direction but can be rotated relatively to each other.

The peripheral outer surface 22 is provided with a flexible ratchet arm 21 which terminates in a steep surface 24. The ratchet arm 21 is on its peripheral surface provided with an outwardly pointing protrusion 25. A part of the steep surface 24 also incorporates the protrusion 25. The protrusion 25 is further provided with a sloped surface 26 which slopes down to the ratchet arm 21 as best seen in FIG. 2.

Once the ratchet tube 20 and the ring 10 is engaged as disclosed in FIG. 2 the steep surface 24 of the ratchet arm 21 engages the steep edge 13 on the ring 10 such that the ratchet tube 20 can only be rotated relatively to the ring 10 in one direction which in FIG. 2 is in the clockwise direction.

Whenever the ratchet tube 20 is rotated in the clockwise direction as indicated with the "dial-up" arrow in FIG. 2 (seen from a proximal position) the torsion spring is strained and is held in this strained position by the engagement between the steep surface 24 of the ratchet arm 21 and the steep edge 13 of the teeth 12 on the ring 10.

In this way a user can strain the torsion spring and thereby set a dose by rotating the ratchet tube 20 relatively to the ring 10 in the clockwise direction and the described engagement 24, 13 makes it impossible for the torsion spring to rotate back the ratchet tube 20.

In order to provide a possibility for the user to dial down the set dose, a reset tube 40 is provided. In relation to FIG. 5, the reset tube 40 is provided with an extended portion 41 which has a forwardly pointing reset element 42 which follows the periphery of the extended portion 41. At its proximal end the reset tube 40 is provided with means 47 for engaging a dose setting button. Alternatively the dose setting button can be integral with the reset tube 40.

Figure 1:
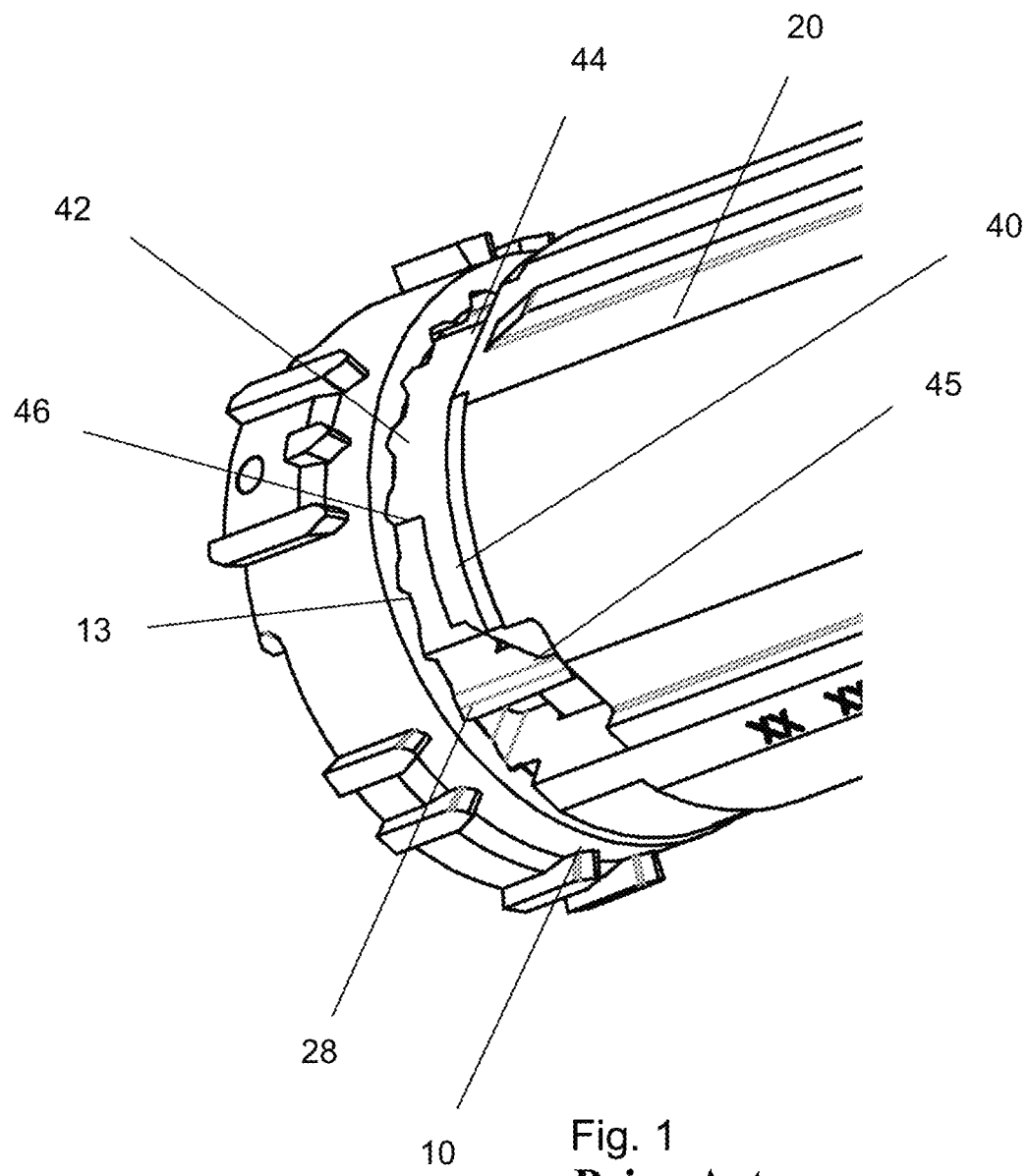
FIG. 1 show an example of a prior art dial-up/dial-down mechanism.

Once the injection device is assembled the reset tube 40 is fitted inside the ratchet tube 20 such that the reset element 42 is located above the ratchet arm 21 as depictured in FIGS. 1 and 2. In this position the axial engagement between the ratchet tube 20 and the reset tube 40 is secured by the protrusion 43 of the reset tube 40 engaging in front of the front surface 29 of the ratchet tube 20.

The extended portion 41 of the reset tube 40 is further provided with a first surface 44 in the clockwise direction and a second surface 45 in the anti-clockwise direction. Further, the reset element 42 is provided with a reset surface 46 in the anti-clockwise direction.

The first surface 44 engages a similar dial-up surface 27 on the ratchet tube 20 such that rotation of the reset tube 40 in the clockwise direction (e.g. in FIG. 2) is transformed directly to the ratchet tube 20 meaning that when a user dials the reset tube 40 in the clockwise direction to set a dose the ratchet tube 20 follows this rotation and rotates relatively to the ring 10.

The second surface 45 engages a spring element 28 urging the reset tube 40 in the clockwise direction whereas the reset surface 46 of the reset element 42 engages the sloped surface 26 of the protrusion 25 of the ratchet arm 21.

When setting a dose as explained above the user rotates the reset tube 40 which rotation is passed on to the ratchet tube 20 which again is allowed to rotate relatively to the ring 10 in the clockwise direction thereby straining the torsion spring.

When a user regrets the set dose and wants to decrease the set dose this is done by rotating the reset tube 40 in the anti-clockwise direction. By doing so—as depictured in FIG. 2—the reset surface 46 is pressed against the sloped surface 26 of the protrusion 25 which pulls the steep surface 24 out of engagement with the steep edge 13 of the tooth 12. This allows the torsion spring to be released and force the ratchet tube 20 rapidly in the anti-clockwise direction under influence of the torque accumulated in the torsion spring. Due to the size of the torque stored in the torsion spring, the ratchet tube 20 will be moved faster than the reset tube 40 whereby the sloped surface 26 of the protrusion 25 will no longer have the pressure of reset surface 46 resting on it and the flexible ratchet arm 21 will flex to its initial position and the steep surface 24 will engage the previous steep edge 13 of the previous tooth 12. By a continued anti-clockwise rotation of the reset tube 40, the steep surface 24 will move from tooth 12 to tooth 12 in a continued movement thereby lowering the torque stored in the torsion spring incrementally.

Once the correct setting is obtained the torque stored in the torsion spring is released by axially moving the ring 10 out of engagement with the housing, whereby the torsion spring rotates back all three elements 10, 20, 40 in the anti-clockwise direction. In the axial movement of the ring 10, it is moved into engagement with a driver which then rotates together with the other elements 10, 20, 40 to drive the piston rod of the system forward.

In order to smoothen the dial-down movement of the ratchet tube 20 and thereby the ratchet arm 21, the ratchet tube 20 is provided with means for establishing a controlled friction between the ratchet tube 20 and the ring 10. These friction means are preferably provided as a number of friction teeth 30 engaging the ring 10 as depictured in FIG. 6 and FIG. 9.

Figure 8:
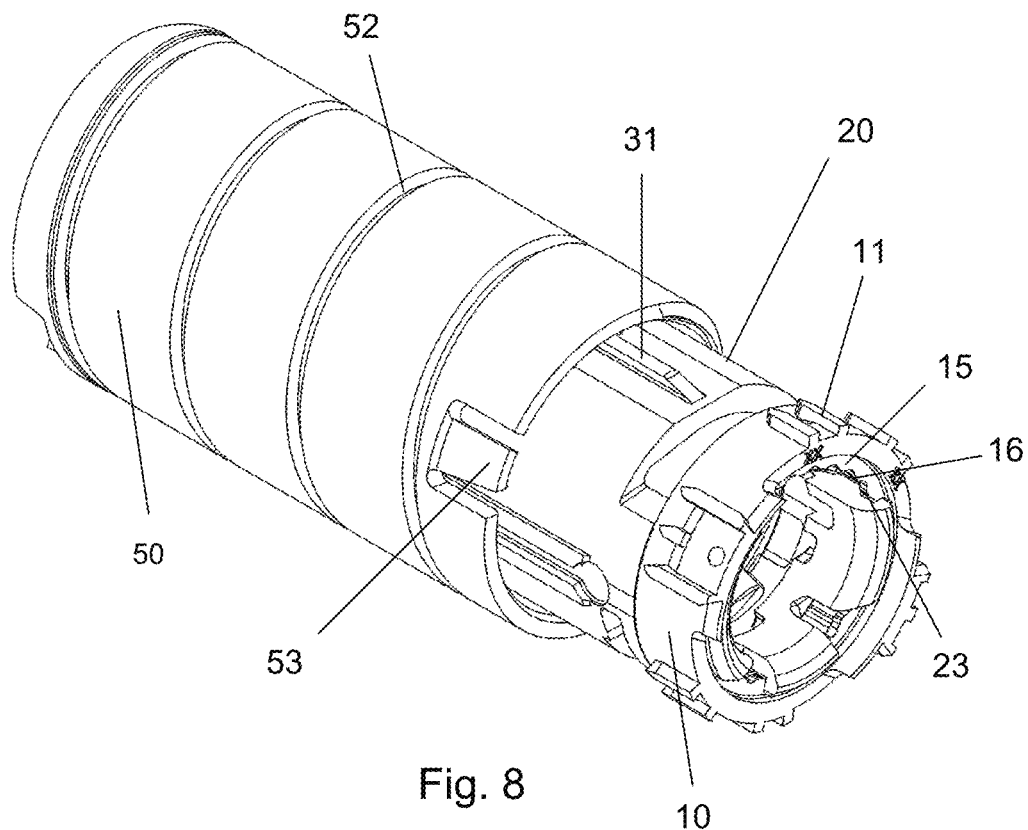
FIG. 8 show a view of the dial-up/dial-down mechanism.
Figure 9:
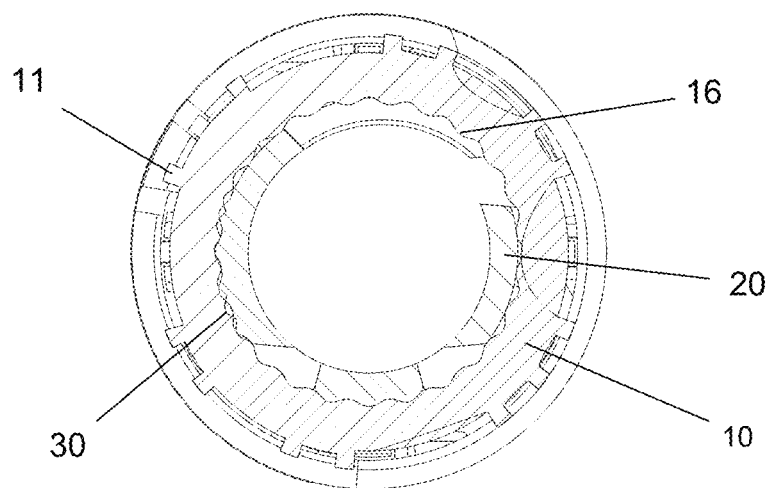
FIG. 9 show a sectional view of the dial-up/dial-down mechanism.

As can be seen in FIG. 8-9, the circular element 15 of the ring 10 engaging the circular recess 23 of the ratchet tube 20 is provided with a cam curve 16. This cam curve 16 is engaged by the friction teeth 30, which friction teeth 30 are provided in the circular recess 23 of the ratchet tube 20.

The ratchet tube 20 is on its outside surface provided with a number of raised ridges 31 stretching axially. These ridges 31 engages a number of similar grooves 51 provided on the inside wall of a dose indicator sleeve 50 which indicator sleeve 50 has indicia printed on its surface for showing the size of the set dose as is commonly known in injection devices.

The dose indicator sleeve 50 is preferably provided with a thread 52 which engages a similar thread i.e. a helical track in the housing such that the dose indicator sleeve 50 moves helically when rotated.

Figure 6:
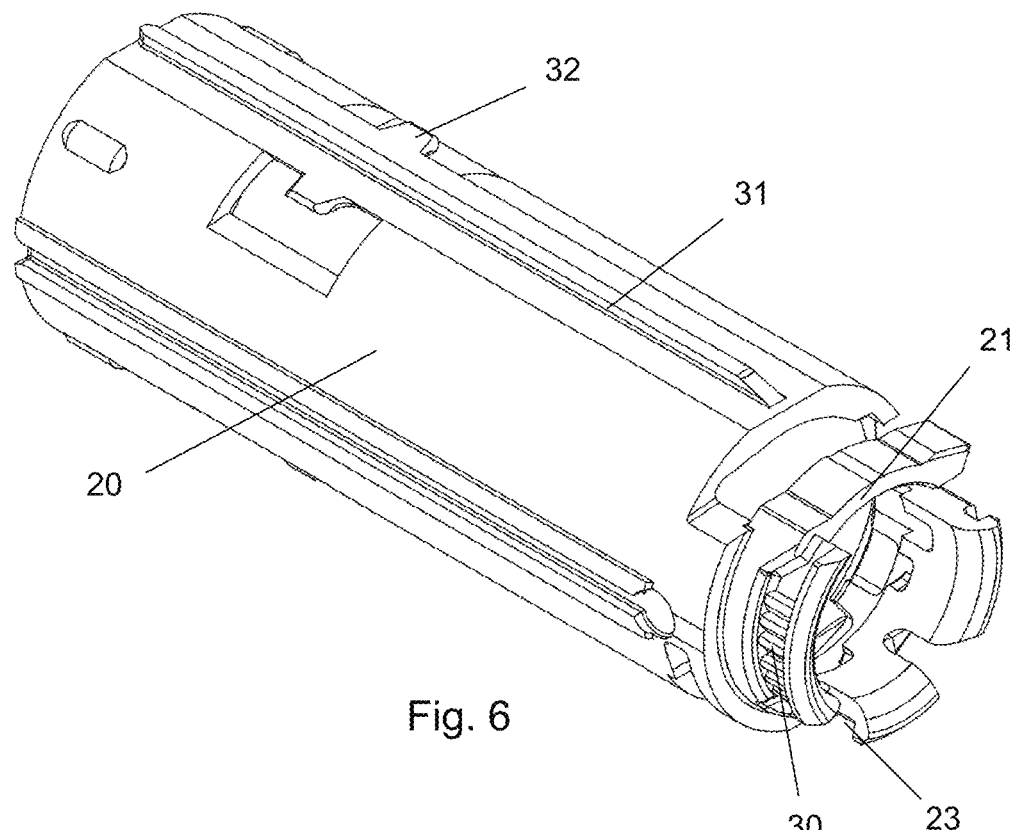
FIG. 6 show a perspective view of the ratchet tube according to the present invention.
Figure 7:
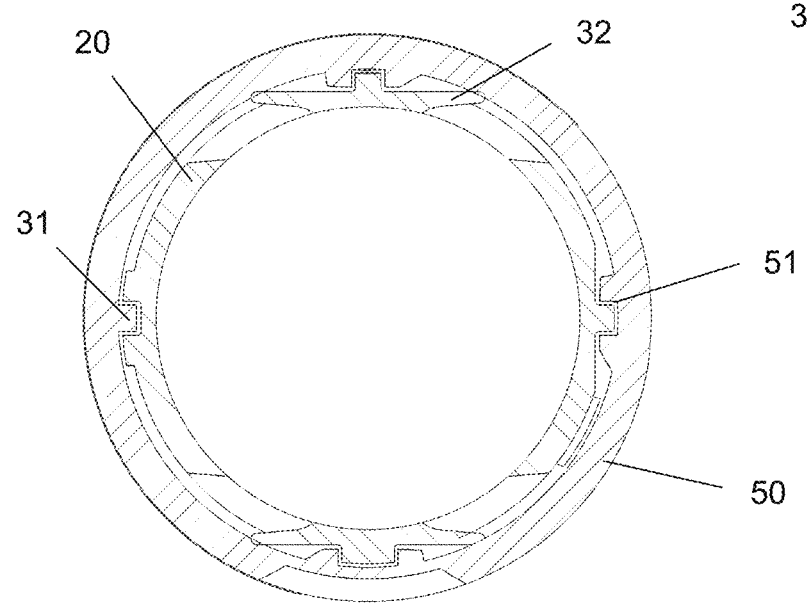
FIG. 7 show a sectional view of the ratchet tube together with the dose indicator sleeve.

In order to prevent this dose indicator sleeve 50 form rattling during rotation, the ratchet tube 20 is further provided with a number of flexible legs 32 which press against the inside surface of the scale drum 50. These legs are best seen in FIG. 6.

Further, additional legs 53 can be provided on the dose indicator sleeve 50 and abutting the ratchet tube 20. These legs can be provided instead of the legs 32 on the ratchet tube 20 or they can be provided in addition to the legs 32.

Whenever the torsion spring moves the ratchet tube 20 in the dial-down direction, the friction teeth 30 makes this rotational movement slightly less rapid which provides a more soft feel to the user as he dials down the set dose, at the same time the flexible legs 32 dampens the rattle of the scale drum 50. Alternatively a set of flexible arms 53 can be provided on the scale drum 50 pressing against the outré surface of the ratchet tube 20.

The friction teeth 30 provide a friction as they slide against the cam curve 16 of the ring element 10, however, the friction dampening can be provided in alternative ways.

Some preferred embodiments have been shown in the foregoing, but it should be stressed that the invention is not limited to these, but may be embodied in other ways within the subject matter defined in the following claims. It must especially be noted that the friction means and the anti-rattling means can be provided simultaneously to the same automatic torsion spring based injection device or they can be applied individually to such injection device.

The invention claimed is:

1. An automatic torsion spring based injection device for multiple injections of a settable and adjustable dose size of a liquid drug comprising:
   a housing holding the liquid drug,
   a rotatable dose setting element comprising a ratchet tube for setting a size of a dose thereby straining a torsion spring, and
   a dial-up/dial-down mechanism;
   wherein the torsion spring is strained when setting the dose by rotating a dose setting element relative to a housing in a first direction and unstrained when rotating the dose setting element in a second direction opposite the first direction,
   the dial-up/dial-down mechanism comprises:
   at least one ratchet arm arranged to follow the rotation of the dose setting element in the first direction when setting a dose,
   a toothed element securing the at least one ratchet arm against a bias of the torsion spring such that engagement of the at least one ratchet arm with a tooth of the toothed element prevents unwinding of the torsion spring, and wherein rotation of the dose setting element in the first direction moves the at least one ratchet arm from one tooth to the subsequent tooth of the toothed element, and rotation of the dose setting element in the second direction lowering the set dose activates the at least one ratchet arm to disengage the teeth of the toothed element and thereby allow the torsion spring to move the at least one ratchet arm in the second direction to the previous tooth such that the force accumulated in the torsion spring reduces incrementally, wherein, the at least one ratchet arm is provided on the ratchet tube which ratchet tube further engages with the toothed element through a plurality of friction teeth thereby dampening a movement of the at least one ratchet arm executed by the torsion spring when the at least one ratchet arm is disengaged from the teeth of the toothed element, and wherein the ratchet tube is provided with structure preventing a dose indicator sleeve from rattling comprising a number of flexible legs provided between the ratchet tube and the dose indicator sleeve.

2. An automatic torsion spring based injection device according to claim 1, wherein the ratchet tube carries the plurality of friction teeth.

3. An automatic torsion spring based injection device according to claim 2, wherein a part of the toothed element engaging the plurality of friction teeth constitutes a cam curve.

4. An automatic torsion spring based injection device according to claim 1, further comprising a reset tube where the reset tube is coupled between the ratchet tube and the dose setting element.

5. An automatic torsion spring based injection device according to claim 1, wherein the ratchet tube is keyed to a dose indicator sleeve by a key and groove connection.

\* \* \* \* \*